United States Patent [19]

Mack

[11] 4,055,182
[45] Oct. 25, 1977

[54] DISPOSABLE DIAPER REINFORCEMENT
[75] Inventor: Robert John Mack, Palatine, Ill.
[73] Assignee: Colgate-Palmolive Company, New York, N.Y.
[21] Appl. No.: 620,733
[22] Filed: Oct. 8, 1975
[51] Int. Cl.$^2$ ............................................. A61F 13/16
[52] U.S. Cl. .................................................. 128/287
[58] Field of Search ............... 128/287, 284, 286, 288, 128/290 R; 428/354; 156/309; 24/DIG. 11

[56] References Cited
U.S. PATENT DOCUMENTS

| 3,612,055 | 10/1971 | Mesek et al. | 128/287 |
| 3,630,201 | 12/1971 | Endres | 128/287 |
| 3,730,798 | 5/1973 | Franz | 128/287 X |
| 3,848,594 | 11/1974 | Buell | 128/284 |
| 3,860,003 | 1/1975 | Buell | 128/287 |
| 3,867,940 | 2/1975 | Mesek et al. | 128/287 |
| 3,900,031 | 8/1975 | Endres et al. | 128/287 |
| 3,913,580 | 10/1975 | Ginocchio | 128/287 X |
| 3,921,639 | 11/1975 | Cepuritis | 128/284 X |
| Re. 26,151 | 1/1967 | Duncan et al. | 128/284 |

Primary Examiner—Clifford D. Crowder
Attorney, Agent, or Firm—Powell L. Sprunger

[57] ABSTRACT

A disposable diaper comprising, an absorbent pad assembly having an absorbent pad, and a relatively thin sheet of flexible material covering a surface of the pad. The diaper has a tape fastener comprising, a pressure-sensitive tape strip having a section secured to an outer surface of the sheet in an area at least partially covering the pad. The diaper also has adhesive means directly bonding the sheet to the pad in a region extending from the area to a location spaced from the area in a direction away from forces normally applied to the strip during placement and use of the diaper.

21 Claims, 9 Drawing Figures

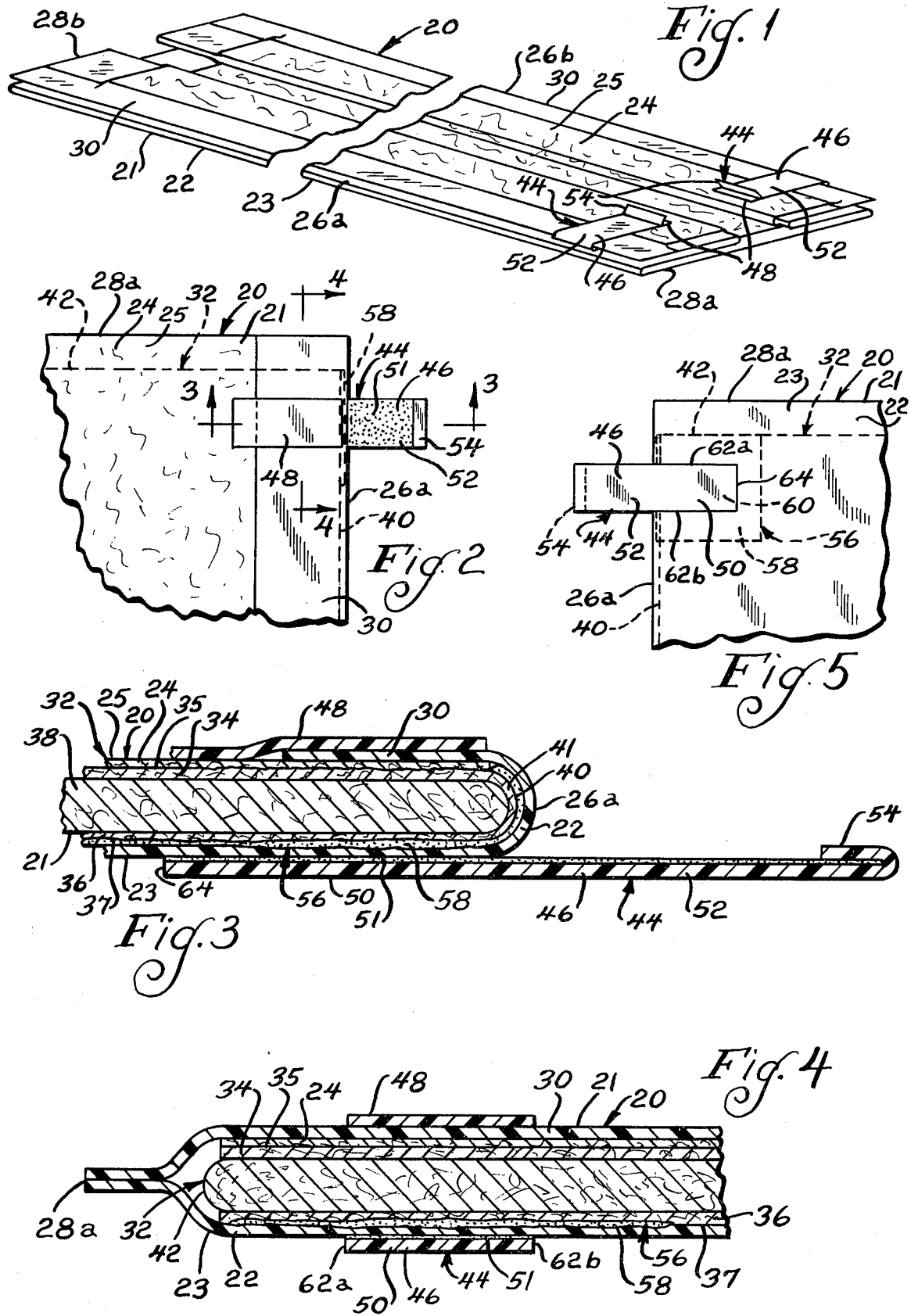

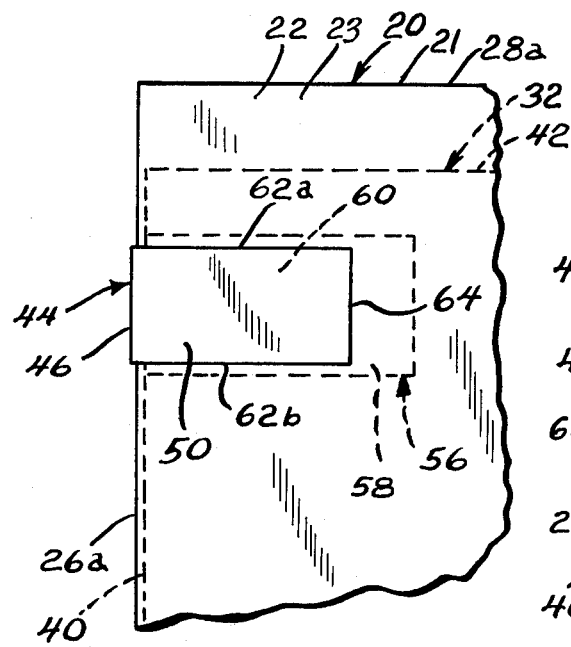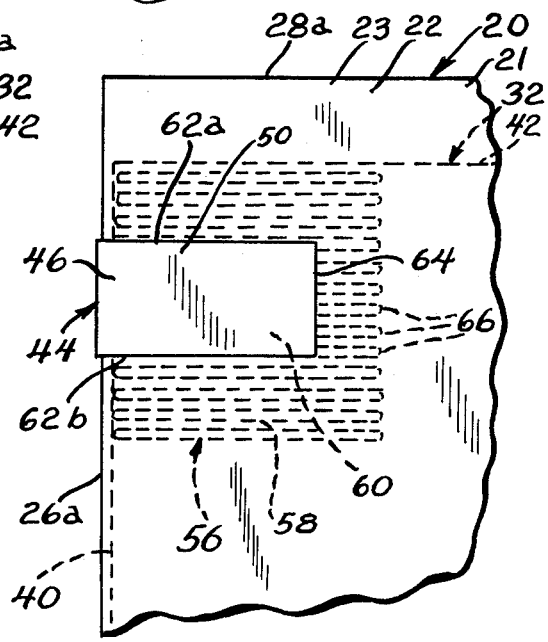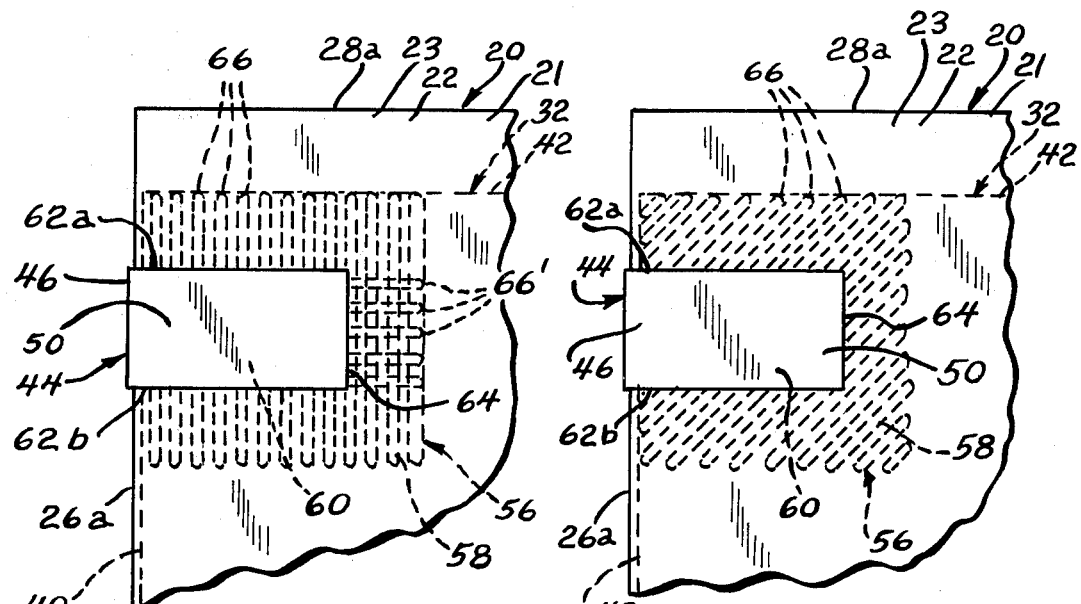

DISPOSABLE DIAPER REINFORCEMENT

BACKGROUND OF THE INVENTION

The present invention relates to absorbent articles, and more particularly to disposable diapers.

In recent years disposable diapers have come into widespread use. Such diapers are normally constructed from an absorbent pad, a fluid impervious backing sheet covering a back surface of the pad, and a fluid pervious top sheet covering a front surface of the pad. The diapers have also been provided with pressure-sensitive tape strips for convenience in placing the diapers on infants. Generally, such tape strips have a first end attached to the backing sheet, and a second securement end which is initially covered by a release sheet and which is fastened to a part of the diaper during placement on the infant.

Since such diapers are discarded after a single use, it is most desirable to make the diapers of economic construction. Accordingly, the backing sheets may be made of a relatively thin plastic material, such as polyethylene having a thickness of approximately 1 mil, in order to reduce its cost, while the thin backing sheets also provide a desirable soft and flexible back surface for the diaper. However, such thin backing sheets do not have high strength characteristics, and when forces are applied against the tape strips, the thin backing sheet can stretch to its yield point, and tear. Thus, the first attached end of the tape strips frequently becomes torn from the backing sheet during placement or use of the diaper. Once the tape strip has been severed from the diaper the diaper may prove worthless, since the torn portion of the backing sheet strongly adheres to the tape strip, and the tape strip cannot normally be repositioned on the diaper.

SUMMARY OF THE INVENTION

A principal feature of the present invention is the provision of a disposable diaper of simplified and economical construction which is reinforced to minimize tearing during application and use.

The diaper of the present invention comprises, an absorbent pad assembly having a pair of side edges, an absorbent pad, and a fluid impervious backing sheet covering at least a portion of a back surface of the pad. The diaper tape fastener comprises, an elongated pressure-sensitive tape strip having an inner section secured to an outer surface of the backing sheet in an area with at least a substantial portion of the section being located over the pad. The diaper also has adhesive means directly bonding the backing sheet to the pad in a region extending from the area to a location spaced inwardly from an inner end of the strip section toward a lateral central part of the pad assembly, with the region including a portion extending substantially the width of the tape section.

A feature of the present invention is that the backing sheet is bonded to the pad by sufficient quantitites of the adhesive means to reinforce and strengthen the backing sheet.

Another feature of the invention is that the reinforced backing sheet prevents tearing of the sheet in the area in which the tape section is attached to the sheet, and thus reinforces the tape fastener.

Yet another feature of the invention is that the adhesive means may be applied in sufficient quantities to bind the back portion of the pad together and thus strengthen this portion of the pad and the reinforcement.

Still another feature of the invention is that in a preferred form the region of the adhesive means extends inwardly past the inner end of the strip section to distribute the forces applied against the tape strip and prevent tearing of the pad adjacent the inner end of the section.

A feature of the invention is that in one form the adhesive means is substantially continuous throughout said region.

Another feature of the invention is that in a preferred embodiment the region extends throughout a substantial portion of the section securement area.

Yet another feature of the invention is that the adhesive means may comprise a plurality of spaced elongated lines of adhesive.

Still another feature of the invention is that the pad may include a back wadding sheet, such that the backing sheet is bonded to the wadding sheet by the adhesive means.

A feature of the invention is that the region may extend around the side edges of the pad assembly to enhance the strength of the reinforcement.

Further features will become more fully apparent in the following description of the embodiments of this invention and from the appended claims.

DESCRIPTION OF THE DRAWINGS

In the drawings:

FIG. 1 is a fragmentary perspective view of a disposable diaper of the present invention;

FIG. 2 is a fragmentary front plan view of the diaper of FIG. 1;

FIG. 3 is a fragmentary sectional view taken substantially as indicated along the line 3—3 of FIG. 2;

FIG. 4 is a fragmentary sectional view taken substantially as indicated along the line 4—4 of FIG. 2;

FIG. 5 is a fragmentary back plan view of the diaper of FIG. 1;

FIG. 6 is a fragmentary back plan view of another embodiment of the diaper of the present invention;

FIG. 7 is a fragmentary back plan view of another embodiment of the diaper of the present invention;

FIG. 8 is a fragmentary back plan view of another embodiment of the diaper of the present invention; and FIG. 9 is a fragmentary back plan view of another embodiment of the diaper of the present invention.

DESCRIPTION OF THE PREFERRED EMBODIMENTS

Referring now to FIGS. 1-5, there is shown a disposable diaper generally designated 20 having an absorbent pad assembly 21. The pad assembly 21 has a fluid impervious backing sheet 22 defining a back surface 23 of the pad assembly 21. The backing sheet 22 may be made of any suitable material, such as polyethylene, and in a preferred form the backing sheet is relatively thin, such as a thickness of approximately 1 mil, to reduce the cost of the diaper and provide a soft and flexible back surface 23. The pad assembly 21 has a fluid pervious cover or top sheet 24, which may be made of any suitable material, such as a nonwoven material, defining a front surface 25 of the pad assembly 21. The pad assembly 21 also has a pair of side edges 26a and 26b, and a pair of end edges 28a and 28b connecting the sides 26a and b. In a preferred form, lateral side margins 30 of the backing sheet 22 are folded over and secured to the front surface 25 of the pad assembly 21.

Referring now to FIGS. 2–5, the pad assembly 21 has an absorbent pad generally designated 32. In a preferred form, the pad 32 has a front sheet 34 of cellulose wadding defining a front surface 35 of the pad 32, a back sheet 36 of cellulose wadding defining a back surface 37 of the pad 32, and an absorbent pad portion 38 of wood fluff located between the front and back wadding sheets 34 and 36, respectively. The front and back wadding sheets 34 and 36 provide structural integrity for the pad portion 38, and prevent breaking up and balling of the pad portion 38 during use of the diaper. As illustrated in FIG. 3, the absorbent pad 32 has side edges 40 which extend to a location adjacent the side edges 26a and b of the pad assembly 21. In a preferred form, the wadding sheets 34 and 36 include a section 41 extending around the side edge of the pad portion 38, as shown. As illustrated in FIG. 4, the backing sheet 22 and top sheet 24 of the pad assembly 21 may be secured together adjacent its end edges 28a and b at a location spaced from end edges 42 of the absorbent pad 32.

As illustrated in FIGS. 1–5, the diaper 20 also has a pair of tape fasteners generally designated 44 to facilitate placement of the diaper on an infant. Each of the tape fasteners 44 have an elongated pressure-sensitive tape strip 46, and a pair of release sheets 48 secured to the front surface 25 of the pad assembly 21. The tape strips 46 have an inner end section 50 permanently secured by adhesive 51 to the back or outer surface 23 of the backing sheet 22, and an outer securement end section 52 which is initially attached to a release surface on the release sheet 48. Thus, the securement end sections 52 are removed from the release sheets 48 preparatory to placement of the diaper on the infant, and the end sections 52 are attached to spaced portions of the diaper during placement to secure the diaper about the infant. The securement end sections 52 may have end tabs 54 to facilitate removal of the end sections 52 from the release sheets 48.

When the outer end sections 52 of the tape strips 46 are removed from the release sheets 48 and located in their outer configuration preparatory to placement of the diaper about the infant, as shown in FIGS. 2, 3, and 5, it will be apparent that forces applied to the strip end sections 52 during and after placement of the diaper are also applied through the inner end sections 50 of the tape strips 46 to the backing sheet 22. Since it is desirable to construct the diapers with relatively thin backing sheets, as previously discussed, such backing sheets frequently become torn by the tape strips when forces are applied to the strips. Once the tape strips 46 have been severed from the backing sheet 22 of the pad assembly, the diapers may be rendered useless, since the torn backing sheet adheres strongly to the tape strip, and the tape strip may not normally be repositioned on the diaper.

In accordance with the present invention, adhesive means generally designated 56, is applied to the inside of the pad assembly, such as the backing sheet, in order to directly bond the inner surface of the backing sheet 22 to the back surface of the back wadding sheet 36 or absorbent pad 32, as illustrated in FIGS. 3–5. The adhesive means 56 may comprise any suitable adherent, binder, or adhesive, such as a water or solvent soluble adhesive, hot melt adhesive or any material suitable for bonding the back sheet to wadding sheet or pad. The adhesive means may be applied through use of suitable techniques, such as gravure printing, roll coating, flow coating, or spraying, and the adhesive may be applied either continuously or in a pattern, as will be seen below.

In a preferred embodiment, the adhesive means 56 extends throughout a region 58 which includes an area 60 over which the inner end section 50 of the tape strip 46 is located. Additionally, the adhesive region 58 preferably extends past opposed sides 62a and 62b of the inner strip section 50, and extends inwardly past an inner end 64 of the strip section 50 toward a lateral central part of the pad assembly or diaper. In the present embodiment, the adhesive 56 is substantially continuous throughout the region 58, and preferably extends 1 inch (2.54 cm.) past each of the strip sides 62a and b, and preferably at least 1 inch (2.54 cm.) inwardly past the inner end 64 of the strip section 50. Thus, if the strip section 50 has a width of approximately 1 inch (2.5 cm.) and a length of approximately 2 inches (5.08 cm.), the region 50 may comprise a space of approximately 9 square inches (58.06 cm.²). Additionally, the region 58 may extend around the side edges 40 of the pad 32, as best shown in FIG. 3. The region is sufficiently saturated with the adhesive means to minimize tearing of the pad assembly in the region.

Thus, in accordance with the present invention the backing sheet 22 is laminated by the adhesive means 56 throughout the region 58 to the back wadding sheet 36 of the absorbent pad 32. When forces are applied against the tape strips 46 of the tape fasteners 44, the forces are distributed by the backing sheet and adhesive means to the wadding sheet throughout the region 58. Accordingly, the wadding sheet increases the effective yield strength of the tape strip attachment to the diaper. The strength of the wadding sheet itself may be selected to have a tearing strength which is suitable for the proposed use of the diaper. For example, a stronger wadding sheet may be selected for diapers which will be utilized on larger infants.

As discussed, the bonding region 58 preferably extends past the area 60 over which the strip section 50 is secured. Particularly, it is desirable that the region 58 extends inwardly past the inner end 64 of the strip section 50, since it has been found that such a configuration dramatically reduces the possibility that the wadding sheet itself may be torn during use of the diaper. If the region 58 terminates at the inner end 64 of the strip section 50, the wadding sheet may tear or rupture inside the pad assembly at a location adjacent the inner end 64 of the strip section 50. Thus, the inner extension of the region 58 causes distribution of forces throughout an inner area of the wadding sheet spaced from the section 50, and greatly enhances the strength of the reinforcement. Further, in a preferred embodiment, the back portion of the wadding sheet is preferably saturated by the adhesive means throughout the region 58, such that the adhesive not only bonds the wadding sheet and backing sheet together, but also acts as a binder for the wadding sheet itself. Accordingly, the adhesive substantially increases the strength of the wadding sheet, which also enhances the strength of the reinforcement to minimize severance of the backing sheet in the area of the strip section 50. In this manner, the ultimate yield strength of the reinforcement is significantly increased over that contributed by the strength of the wadding and backing sheets alone. The extension of the region 58 around the side edge of the pad effectively joins the region to the front portion of the diaper, and further enhances the yield strength of the reinforcement. The adhesive means may be applied at a minimal cost and inconvenience with high speed manufacturing equipment to make the diapers of the present invention.

Another embodiment of the present invention is illustrated in FIG. 6, in which like reference numerals designate like parts. In this embodiment, the region 58 of the adhesive means 56 extends inwardly from the inner end 64 of the strip section 50, and extends only slightly past the sides 62a and b of the strip section 50, as shown. Also, in this embodiment the adhesive means 56 is substantially continuous throughout the region 58.

Another embodiment of the diaper of the present invention is illustrated in FIG. 7, in which like reference numerals designate like parts. In this embodiment the adhesive means 56 comprises a plurality of elongated spaced lines 66 of adhesive which bond the backing sheet to the back wadding sheet in the region 58. In this embodiment, the adhesive lines 66 are generally aligned with the elongated tape strip section 50. As before, the region 58 of spaced lines 66 extends past the sides 62a and b of the strip section 50, and extends inwardly from the inner end 64 of the strip section 50.

Another embodiment of the diaper of the present invention is illustrated in FIG. 8, in which like reference numerals designate like parts. In this embodiment, the spaced adhesive lines 66 extend generally at right angles to the strip section 50 throughout the region 58. In a preferred form, the adhesive means 56 also includes adhesive 66', such as a plurality of spaced lines, as shown, extending from the area 60 beneath the strip section 50 to an inner part of the bonding region 58. The adhesive lines 66' connect the lines 66 and prevent tearing of the wadding sheet intermediate the spaced line 66 at a location inwardly of the inner end 64 of the strip section 50.

Another embodiment of the diaper of the present invention is illustrated in FIG. 9, in which like reference numerals designate like parts. In this embodiment, the spaced adhesive lines 66 extend at an acute angle, such as approximately 45°, relative the strip section 50. The lines 66 may extend diagonally in either direction throughout the adhesive region 58, as desired.

The foregoing detailed description is given for clearness of understanding only, and no unnecessary limitations should be understood therefrom, as modifications will be obvious to those skilled in the art.

I claim:

1. A disposable diaper, comprising:
an absorbent pad assembly having an absorbent pad, and a relatively thin sheet of flexible material covering a surface of said pad;
a tape fastener comprising, a pressure-sensitive tape strip having a section secured to an outer surface of said sheet in an area at least partially covering said pad, and a securement portion adapted to extend past a side edge of the pad assembly for securing the diaper about an infant; and
adhesive means directly bonding said sheet to said pad surface in an isolated region overlapping a major portion of the area and extending beyond said area to a location spaced from the area in a direction away from forces normally applied to the strip during placement and use of the diaper, said region including a portion extending substantially the width of said tape section in said area and being sufficiently saturated to reinforce the pad adjacent said surface and minimize tearing of the pad assembly in said region.

2. The diaper of claim 1 wherein said sheet comprises a backing sheet of fluid impervious material covering at least a portion of a back surface of said pad, said strip section is secured to an outer surface of said backing sheet with at least a substantial portion of said section being located over said pad, and in which the adhesive means directly bonds said backing sheet to the pad surface such that the region extends to a location spaced inwardly from an inner end of the strip section toward a lateral central part of the pad assembly.

3. The diaper of claim 2 wherein said adhesive means is substantially continuous throughout said region.

4. The diaper of claim 2 wherein a sufficient quantity of the adhesive means is applied to the diaper to strengthen the back surface of the pad in said region.

5. The diaper of claim 2 wherein said region extends substantially throughout said area.

6. The diaper of claim 2 wherein said region extends past at least one side of said section.

7. The diaper of claim 6 wherein said region extends past both sides of said section.

8. The diaper of claim 7 wherein said region extends at least 1 inch (2.54 cm.) past both sides of said section.

9. The diaper of claim 2 wherein said region extends at least 1 inch (2.54 cm.) from the inner end of said section toward the lateral central part of the pad assembly.

10. The diaper of claim 2 wherein said region comprises a plurality of spaced elongated lines of said adhesive means.

11. The diaper of claim 10 wherein said lines are generally aligned with said strip section.

12. The diaper of claim 10 wherein said lines are disposed at an acute angle relative the length of said strip section.

13. The diaper of claim 10 wherein said lines are disposed generally at right angles relative the length of said strip section.

14. The diaper of claim 13 wherein the adhesive means includes a portion connecting an inner set of said lines.

15. The diaper of claim 2 wherein said pad includes a back wadding sheet, and in which said adhesive means secures the backing sheet to said wadding sheet.

16. The diaper of claim 2 wherein the pad includes a pair of side edges, the side edges of said pad are located adjacent side edges of the pad assembly, and said area is located adjacent the side edges of the pad assembly.

17. The diaper of claim 16 wherein said backing sheet and region extends around the side edges of the pad.

18. The diaper of claim 17 wherein said pad includes at least one wadding sheet defining the side edges of the pad, and in which the adhesive means secures the backing sheet to said wadding sheet.

19. The diaper of claim 2 wherein the pad assembly has a pair of side edges, the pad has a pair of side edges located adjacent the side edges of the pad assembly and a back wadding sheet, the backing sheet covers a back surface of the pad wadding sheet, said strip section comprises an inner section fixedly attached to the backing sheet adjacent one side edge of the pad assembly with a substantial portion of the section being located in said area over the wadding sheet, and the adhesive means directly bonds the backing sheet to the wadding sheet in a substantially continuous region extending throughout a substantial portion of said area.

20. A disposable diaper, comprising:
- an absorbent pad assembly having an absorbent pad, a fluid pervious top sheet, and a backing sheet of fluid impervious material covering at least a portion of a back surface of the pad and extending around a side edge of the pad;
- a tape fastener comprising, an elongated pressure-sensitive tape strip having a section secured to an outer surface of said backing sheet in an area with at least a substantial portion of said section being located over said pad, and a securement portion adapted to extend past a side edge of the pad assembly for securing the diaper about an infant; and
- adhesive means directly bonding said backing sheet to said pad in a region overlapping a major portion of the area and extending beyond said area around said side edge of the pad, said adhesive means being saturated in a sufficient quantity to reinforce the pad and minimize rupture of the backing sheet.

21. The diaper of claim 20 wherein said pad includes a wadding sheet defining said side edge of the pad.

* * * * *